United States Patent [19]

Vinegar et al.

[11] Patent Number: 4,613,754
[45] Date of Patent: Sep. 23, 1986

[54] TOMOGRAPHIC CALIBRATION APPARATUS

[75] Inventors: Harold J. Vinegar; Scott L. Wellington, both of Houston, Tex.

[73] Assignee: Shell Oil Company, Houston, Tex.

[21] Appl. No.: 566,617

[22] Filed: Dec. 29, 1983

[51] Int. Cl.$^4$ .............................................. G01D 18/00
[52] U.S. Cl. .................................... 250/252.1; 378/201
[58] Field of Search ................. 250/252.1; 378/18, 201

[56] References Cited

U.S. PATENT DOCUMENTS 4,029,963  6/1977  Alvarez et al. ........................ 250/367
4,233,507  11/1980  Volz ....................................... 378/18

Primary Examiner—Janice A. Howell

[57] ABSTRACT

An apparatus for providing data for the calibration of the atomic number and density of a test material being scanned in the radiation field of a computerized axial tomographic scanner (CAT). The apparatus comprises a housing which is adapted to be positioned in the X-ray field of the CAT in a predetermined position. The housing has an aperture that is adapted to accommodate the test material, and a plurality of calibration materials which have known atomic numbers and densities are positioned in the housing. In addition, the present invention provides a calibration apparatus that has a surface that is adapted to accommodate the test material.

19 Claims, 9 Drawing Figures

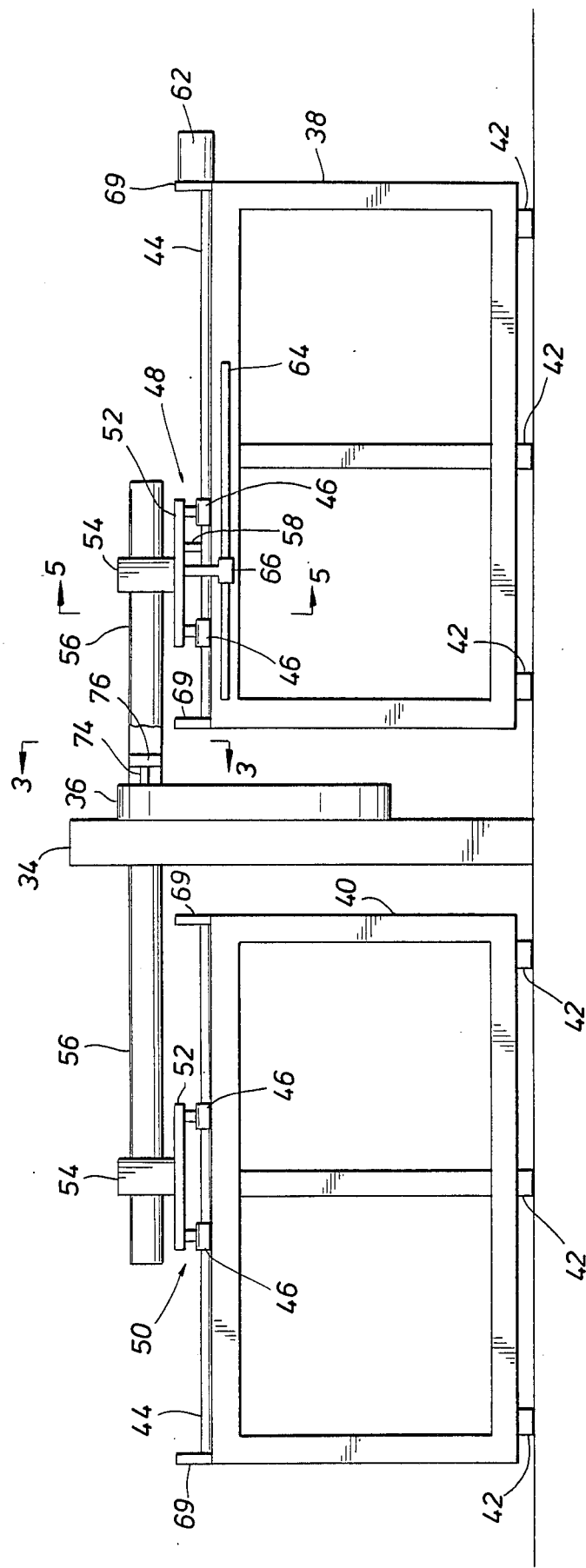
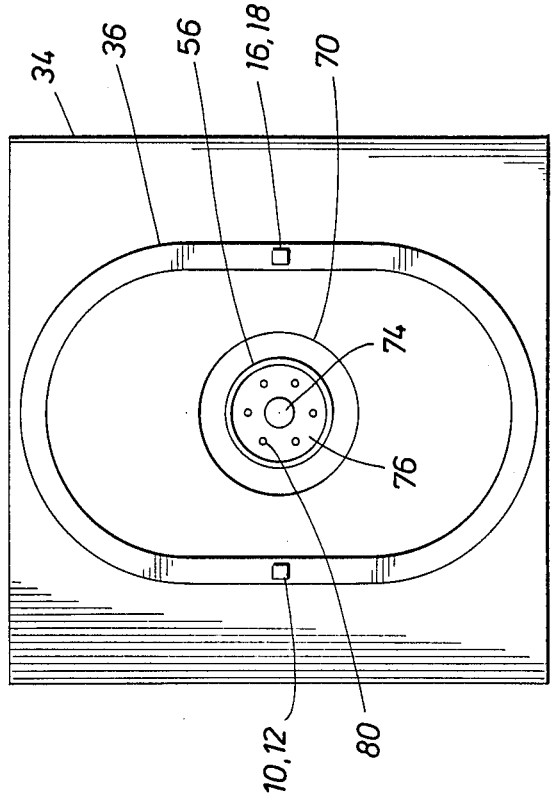
FIG. 2
FIG. 3

TOMOGRAPHIC CALIBRATION APPARATUS

BACKGROUND OF THE INVENTION

This invention relates to computerized axial tomographic analysis.

SUMMARY OF THE INVENTION

In accordance with present invention there is provided an apparatus for providing data for the calibration of the atomic number and density of a test material being scanned in the radiation field of a computerized axial tomographic scanner, hereinafter referred to as "CAT." The apparatus comprises a housing which is adapted to be positioned in the X-ray field of the CAT in a predetermined position. The housing has an aperture that is adapted to accommodate the test material, and a plurality of calibration materials which have known atomic numbers and densities are positioned in the housing. In addition, the present invention provides a calibration apparatus that has a surface that is adapted to accommodate the test material.

The calibration phantom of the present invention allows scanning of calibration or reference materials simultaneously with the scanning of the material under test, thereby providing proper calibration and compensation for the various attenuation characteristics of different test samples. Moreover, the calibration materials are always positioned in a predetermined location in the X-ray field thereby simplifying the software necessary to process the data from the calibration materials. The calibration phantom can take various embodiments. For example, if a core sample from a borehole is to be analyzed, the housing of the calibration phantom can be a cylinder which has an aperture that is sized to accommodate the core sample or the container in which the core sample is located, and if a human body is to be analyzed, the housing can be the table on which the patient lies. The calibration materials can be rods, vials or other suitable containers positioned in the housing. The calibration materials should be at least as long as the material to be tested and should include materials that are expected to be in the material under test. In addition, the calibration materials should have known densities and effective atomic numbers.

Other objectives, advantages and applications of the present invention will be made apparent by the following detailed description of the preferred embodiments of the present invention.

BRIEF DESCRIPTION OF THE DRAWINGS

FIG. 2 is a side view of the sample holding apparatus employed with the computerized axial tomographic analyzer.

FIG. 3 is a cross sectional view taken along lines 3—3 of FIG. 2.

DETAILED DESCRIPTION OF THE PREFERRED EMBODIMENTS

Figure 1:
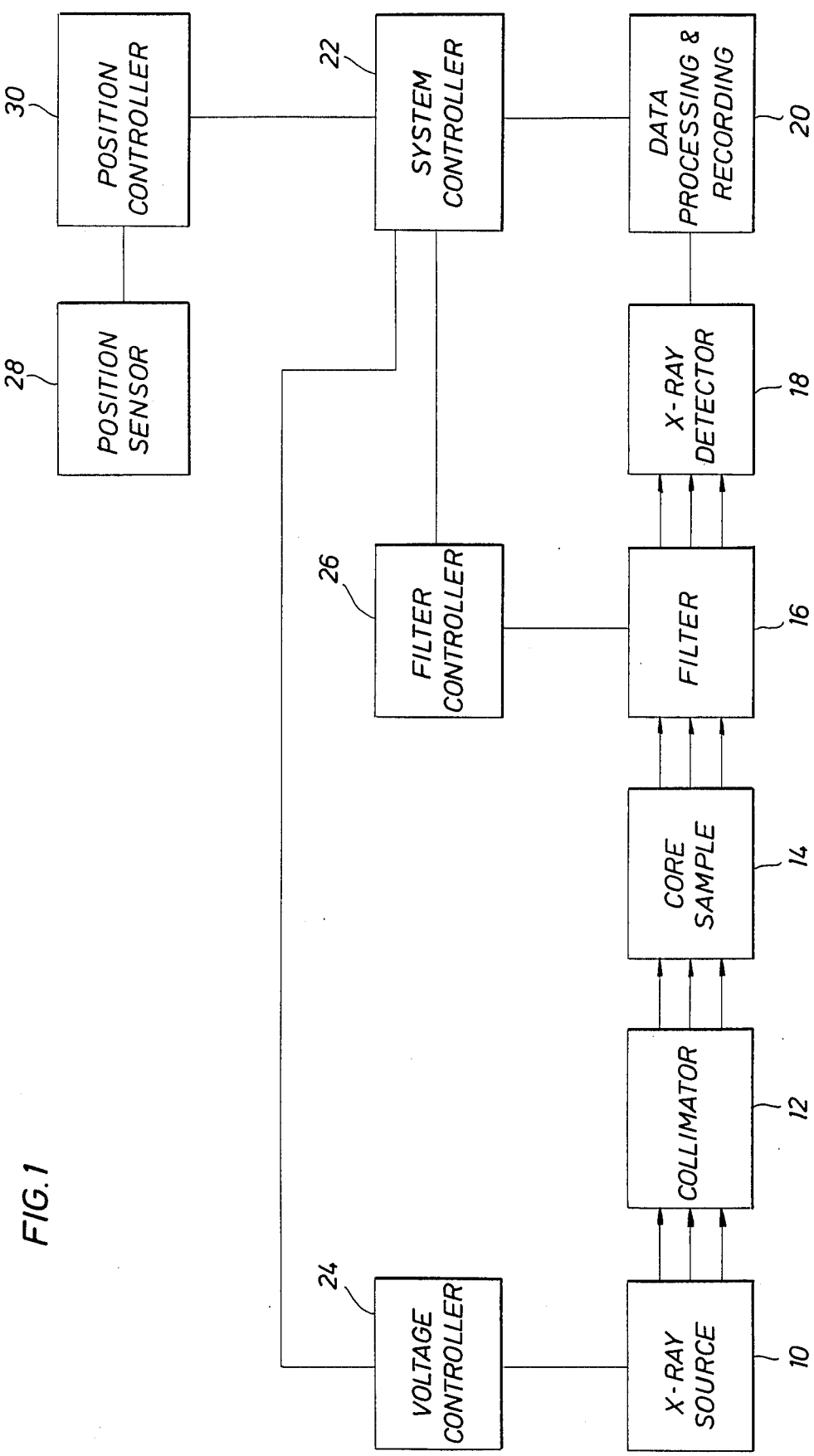
FIG. 1 is a block diagram of a computerized axial tomographic analyzer in which the present invention can be incorporated.
Figure 4:
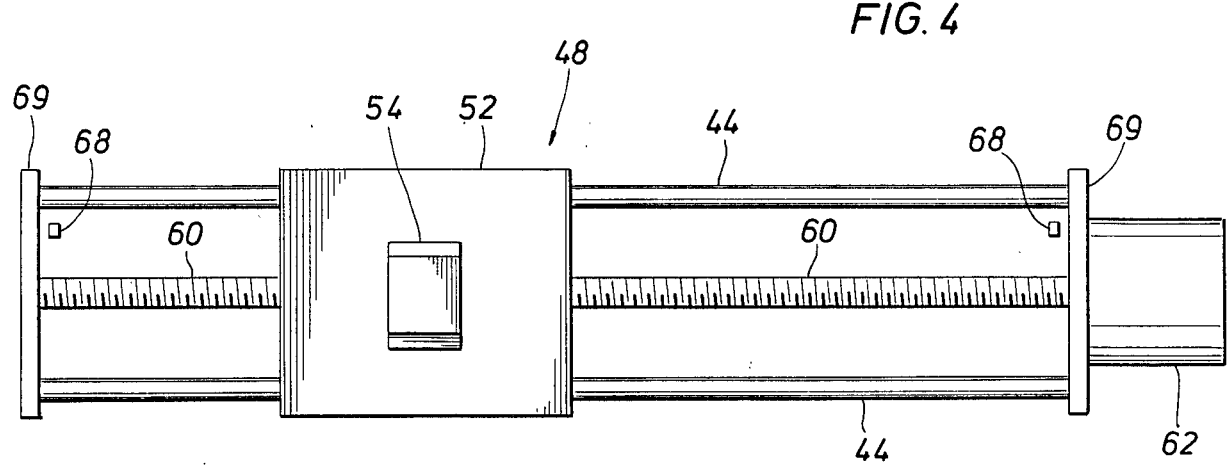
FIG. 4 is a top view of the motorized side of the sample holding apparatus.
Figure 5:
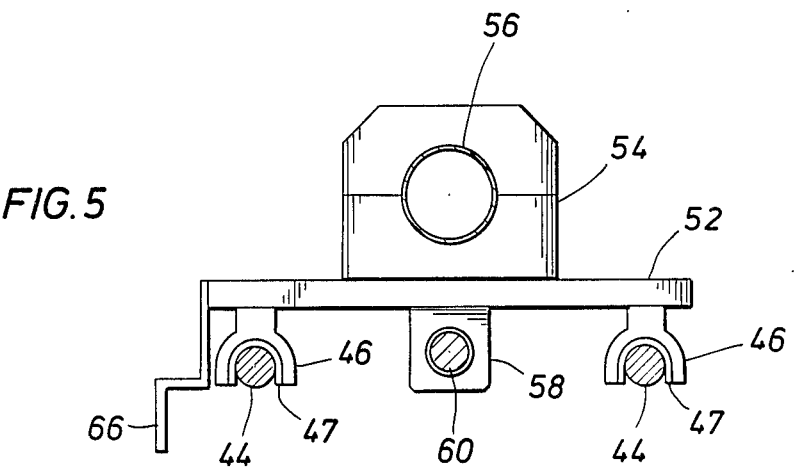
FIG. 5 is a cross sectional view taken along lines 5—5 of FIG. 2.
Figure 6:
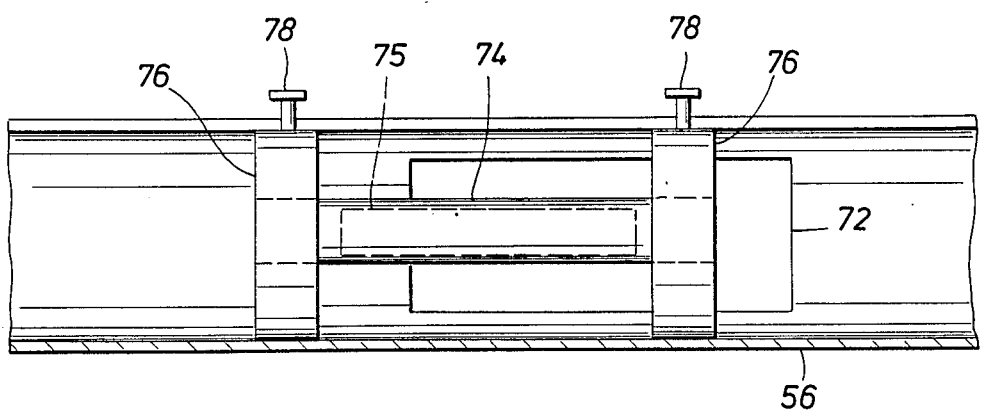
FIG. 6 is a side view of the tube and cylinder portion of the sample holding apparatus.

Referring to FIG. 1, a typical CAT in which the present invention can be utilized employs an X-ray source 10 to provide X-rays which are indicated by a plurality of arrows; these X-rays are collimated by collimator 12 prior to passing through core sample 14. After the X-rays have passed through core sample 14, they are filtered by filter 16 which can be, for example, air, tungsten or copper. Alternatively, filter 16 can be applied to the X-rays prior to their entering core sample 14 rather than after their passage through core sample 14. The filtered X-rays are then detected by X-ray detectors 18 which generate signals indicative thereof; these signals are provided to suitable data processing and recording equipment 20. The entire operation, from the generation of the X-rays to the processing of the data is under the control of system controller 22. Suitable signals are provided by system controller 22 to voltage controller 24 which controls the voltage applied to X-ray source 10, thereby controlling the energy range of the X-rays. Alternatively, filter 16 can be used to vary the energy range as is known in the art. System controller 22 also provides suitable control signals to filter controller 26 to apply the appropriate filter to the X-rays which have passed through core sample 14 before they are detected by X-ray detector 18. The point along core sample 14 that is being analyzed is detected by sample position sensor 28 which provides signals indicative thereof to sample position controller 30. System controller 22 provides signals which are indicative of the desired point along core sample 14 or the amount of advancement from the last point analyzed, to sample position controller 30, which moves core sample 14 to the proper location.

Referring now to FIGS. 2–6, a suitable CAT and sample positioning system for use with the present invention is shown in detail. A typical CAT, for example, the Deltascan-100 manufactured by Technicare Corporation of Clevelend, Ohio is indicated by numeral 34. CAT 34 has a gantry 36 which contains X-ray source 10, collimator 12, filter 16 and X-ray detectors 18. Support structures or tables 38 and 40 are located on opposite sides of CAT 34 and have legs 42 which are suitably attached to, for example, the floor, to ensure that tables 38 and 40 maintain proper positioning and alignment with CAT 34. Tables 38 and 40 each have a set of guide means or rails 44, such as one inch diameter solid 60 case shafts mounted on shaft supports, Model No. SR-16, both being manufactured by Thomson Industries, Inc. of Manhasset, N.Y., on which the legs 46 of trolleys 48 and 50 ride. Preferably, legs 46 have a contact portion 47 that includes ball bearings in a nylon enclosure, such as the Ball Bushing Pillow Block, Model No. PBO-16-OPN, which are also manufactured by Thomson. Trolleys 48 and 50 have flat member 52 which is attached to legs 46 such that member 52 is parallel to rails 44. A member 54 which can consist of two pieces fastened together by suitable means, such as screws, is mounted on member 52 and has an aperture suitable for holding tube 56. Member 52 of trolley 48 has a member 58 attached to the bottom portion of member 52 that is provided with suitable screw threads for mating with gear or screw 60. Screw 60 is driven by motor 62 for moving trolley 48 horizontally. Screw 60 can be, for example, a preloaded ball bearing screw, Model No. R-0705-72F-W, manufactured by Warner Electric Brake & Clutch Company of Beloit, Wis., and motor 62 can be, for example, a DC motor, Model No. 1165-01DCMO/E1000MB/X2, marketed by Aerotech, Inc. of Pittsburg, Pa. Motor 62 turns a predetemined number of degrees of revolution in response to a signal from sample position controller 30 of FIG. 1, which can be, for example, a Unidex Drive, Model No. SA/SL/C/W/6020/DC-0/F/BR/R*, which is also marketed by Aerotech. Table 38 and trolley 48 also contain an optical encoding position sensing system, for example, the Acu-Rite-II manufactured by Bausch and Lomb Company of Rochester, N.Y., which comprises a fixed ruler or scale 64 attached to table 38 and an eye or sensor 66 attached to member 52 of trolley 48 for determining the position along ruler 64 at which trolley 48 is located. The digital output from optical sensor 66 is provided to sample position controller 30 of FIG. 1 so that sample position controller 30 can compare this with the desired position indicated by digital signal from system controller 22 and provide appropriate control signals to motor 62 for rotation of screw 60 to accurately position trolley 48. Table 38 can also be provided with limit switches 68 which provide appropriate control signals to sample position controller 30 which limits the length of travel of trolley 48 from hitting stops 69 on table 38.

Tube 56 is centered in the X-ray field 70 of CAT 34. The attachment of tube 56 to members 54 of trolley 48 and 50 by a screw or other suitable fastening means causes trolley 50 to move when trolley 48 is moved by means of screw 60 and motor 62. Tube 56 which preferably is made of material that is optically transparent and mechanically strong and has a low X-ray absorption, for example, plexiglas, has a removable window 72 to facilitate the positioning of sample holder 74 in tube 56. A core sample 75 is positioned in sample holder 74 as indicated by dotted lines. The ends of sample holder 74 are positioned in central apertures of discs 76, which can be made of a low friction material, for example, nylon, and are sized such that they make a close sliding fit to ensure centering of the sample inside tube 56. Discs 76 are locked in position in tube 56 by screws 78 which can be made of, for example, nylon. In addition, discs 76 can be provided with a plurality of apertures 80 sized to accommodate fluid lines and electrical power lines from various equipment associated with sample holder 74.

Sample holder 74 can be pressure-preserving, core-sample container used in normal coring operations; however, if standard X-ray energy associated with CAT scan analytic equipment, such as the Deltascan-100 mentioned hereinabove, the pressure vessel must be made of material that will allow the X-rays to pass through the container walls, for example aluminum, beryllium or alumina. Aluminum is preferred because it absorbs a portion of the low energy spectra, thus making the beam more monochromatic. Nevertheless, steel pressure containers can be employed if higher energy X-ray tybes or radioactive sources are used. In the case of a frozen core sample the container can be positioned inside an insulating cylinder which can be made of, for example, styrofoam or other insulating materials with low X-ray absorption. This insulating cylinder can be filled with dry ice or the like to keep the core sample frozen. If it is desired to heat a core sample, a heating element which has a low X-ray absorption, such as the heating foil manufactured by Minco Products, Inc. of Minneapolis, Minn., can be wrapped around the container to heat the sample and a similar insulating cylinder can be used. CAT scans are performed at two different X-ray tube energies. One scan is performed at an energy that is low enough to be predominantly in the photoelectric region, that is, less than approximately 80 keV mean energy, and the other scan is performed at an energy that is high enough to be predominantly in the Compton region, that is, greater than approximately 80 KeV mean energy. Either pre-imaging or post-imaging techniques can be applied to the attenuation coefficients obtained by the dual energy scans to determine the effective atomic number of the core sample. For example, the techniques of Alvarez et al, U.S. Pat. No. 4,029,963, can be used to determine the effective atomic numbers for the plurality of points in each cross section. Preferably, the effective atomic numbers and densities are determined according to the method described hereinbelow. However, it should be noted that the method described hereinbelow is provided for illustration and not limitation, since the calibration apparatus of the present invention can be used with any method for calibrating the density and/or effective atomic number of the material being analyzed.

The energy dependence of the X-ray linear attenuation coefficient $\mu$ is separated into two parts:

$$\mu = \mu_p + \mu_c \tag{1}$$

where $\mu_c$ is the Klein-Nishina function for Compton scattering multiplied by electron density, and $\mu_p$ represents photoelectric aborption (including coherent scattering and binding energy corrections). The photoelectric and Compton contributions are expressed in the form:

$$\mu = a Z^m \rho + b\rho \tag{2}$$

where Z is the atomic number, m is a constant in the range of 3.0 to 4.0, $\rho$ is the electron density, and a and b are energy-dependent coefficients. It should be noted that the specific choice of m depends upon the atomic numbers included in the regression of the photoelectric coefficients. Equation (2) depends on the fact that the energy dependence of the photoelectric cross section is the same for all elements.

For a single element, Z in equation (2) is the actual atomic number. For a mixture containing several elements, the effective atomic number $Z^*$ is defined as:

$$Z^* = \sqrt[m]{\sum_i f_i Z_i^m} \tag{3}$$

where $f_i$ is the fraction of electrons on the $i^{th}$ element of atomic number $Z_i$, relative to the total number of electrons in the mixture, that is, $$f_i = \frac{n_i Z_i}{\sum_i n_i Z_i} \tag{4}$$

where $n_i$ is the number of moles of element i.

The method consists of utilizing a CAT to image a core sample at a high and low X-ray energy level. The energies are chosen to maximize the difference in photoelectric and Compton contributions while still allowing sufficient photon flux to obtain good image quality at the lower X-ray energy. Letting 1 and 2 denote the high and low energy images and dividing equation (2) by $\rho$, the following relationships are obtained $$\mu_1/\rho = a_1 Z^3 + b_1 \quad (5a)$$

$$\mu_2/\rho = a_2 Z^3 + b_2 \quad (5b)$$

Energy coefficients ($a_1$, $b_1$) and ($a_2$, $b_2$) are determined by linear regression of $\mu/\rho$ on $Z^3$ for the high and low energy images, respectively, of calibration materials with a range of known atomic numbers and densities. Once ($a_1$, $b_1$) and ($a_2$, $b_2$) are determined, a material of unknown electron density, $\rho_x$, and effective atomic number, $Z_x^*$, can be analyzed in terms of the measured attenuation coefficients $\mu_{1x}$, $\mu_{2x}$:

$$\rho_x = \frac{a_1 \mu_{2x} - a_2 \mu_{1x}}{(a_1 b_2 - a_2 b_1)} \quad (6a)$$

$$Z_x^* = \sqrt[3]{\frac{1}{a_1} \frac{(\mu_{1x} - b_1)}{\rho}} = \sqrt[3]{\frac{-b_1 \mu_{2x} + b_2 \mu_{1x}}{a_1 \mu_{2x} - a_2 \mu_{1x}}} \quad (6b)$$

Equations (5a) and (5b) are applied to each corresponding pixel of the high and low energy images; these computations can be performed on a minicomputer or other suitable means.

Figure 7:
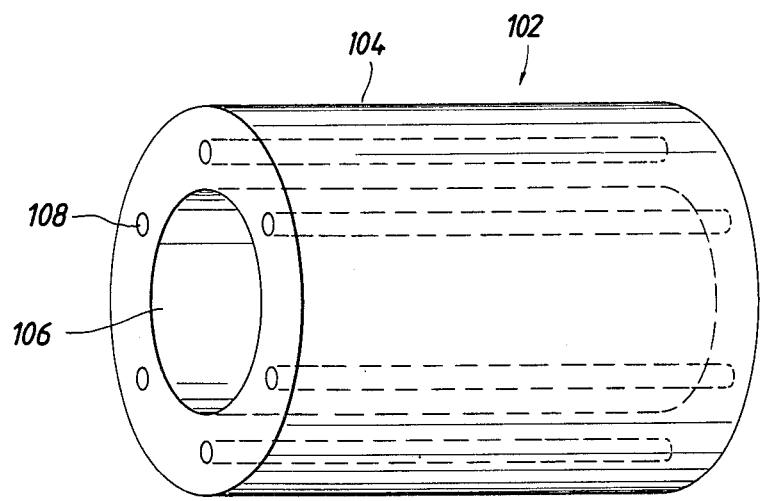
FIG. 7 illustrates one embodiment of the calibration phantom of the present invention.

FIG. 7 illustrates one embodiment of the calibration of the present invention. Calibration phantom 102 consists of a cylinder 104 which has an aperture 106 that is suitably sized for holding a sample or sample container. Cylinder 104 which can be made of, for example, plexiglas or other suitable material having low X-ray absorption, contains a plurality of vials or rods 108. Vials or rods 108 should contain or be made of material that is expected to be found in the sample under test. The calibration materials in vials or rods 108 have known densities and effective atomic numbers and should be at least as long as the sample under test. In the case of a core sample rods 108 can be made of aluminum, carbon, fused quartz, crystalline quartz, calcium carbonate, magnesium carbonate and iron carbonate. Referring to FIGS. 2-7, cyclinder 104 can be positioned around tube 56 or it can be an integral part of tube 56. Still further, it can be an integral part of sample holder 74 or positioned in some other known relation in X-ray field 70. It should be noted that calibration phantom 102 is scanned at the same time that the sample is scanned.

Figure 8B:
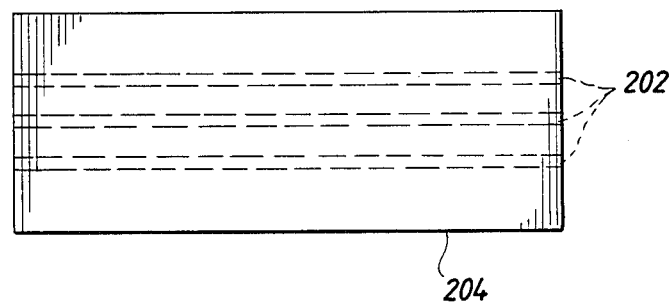
FIGS. 8A and 8B illustrate an alternative embodiment of the calibration phantom of the present invention.
Figure 8A:
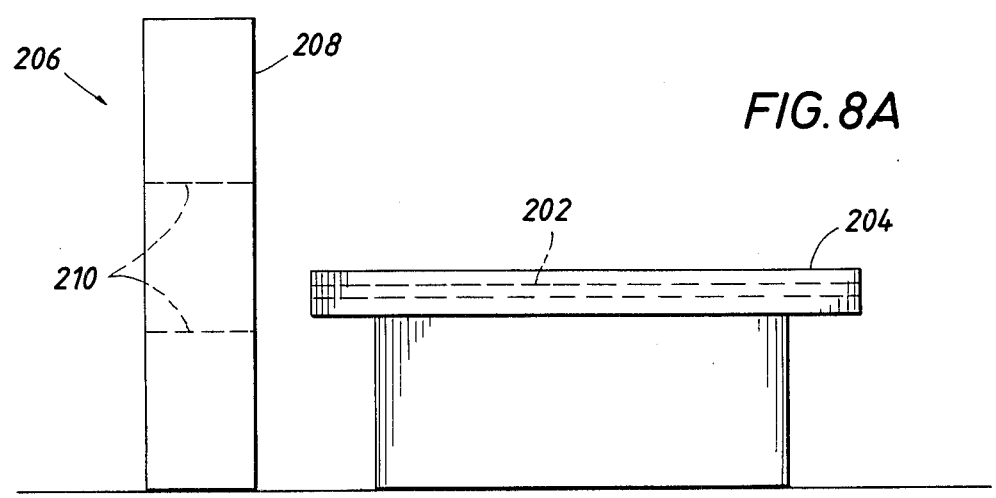

FIGS. 8A and 8B illustrate an alternative embodiment of the calibration phantom of the present invention. In this embodiment the calibration rods or vials 202 are positioned in a movable support structure or table 204, such as the Patient Couch for use with the Synerview CT Systems 600S and 1200SX which is manufactured by Picker International Inc. of Highland Heights, Ohio. CAT 206 is shown with a typical shroud 208 which covers all of the internal mechanisms associated with CAT 206. The X-ray field of CAT 206 is indicated by dotted lines 210. Table 204 is movable as is known in the art and can be sized for use with human patients or any other test material. Calibration rods or vials 202 should be at least as long as the test material to be scanned and, preferably, should be about as long as table 204. Calibration rods or vials 202 should be made of or contain materials that are expected to be in the material under test and that have a known density and effective atomic number. For example, if a human body is to be scanned calibration vials could contain solutions of water with dissolved salts of sodium, calcium, iron and so forth.

It is to be understood that variations and modifications of the present invention can be made without departing from the scope of the invention. It is also to be understood that the scope of the invention is not to be interpreted as limited to the specific embodiments disclosed herein, but only in accordance with the appended claims when read in light of the foregoing disclosure.

What is claimed is:

1. An apparatus for providing data for the calibration of the atomic number and density of a test material being scanned in the radiation field of a computerized axial tomographic scanner, said apparatus comprising: a housing adapted to be positioned in said radiation field in a predetermined position and having an aperture adapted to accommodate said test material; and a plurality of calibration materials having known atomic numbers and densities positioned in said housing.

2. An apparatus as recited in claim 1, wherein said plurality of calibration materials comprises a plurality of rods.

3. An apparatus as recited in claim 1, wherein said plurality of calibration materials comprises a plurality of vials containing a plurality of fluids.

4. An apparatus as recited in claim 1, wherein said predetermined position of said housing is stationary within said radiation field and said test material is moveable.

5. An apparatus as recited in claim 1, wherein said plurality of calibration materials are at least as long as said test materials.

6. An apparatus as recited in claim 1, wherein said housing comprises a cylinder.

7. An apparatus as recited in claim 1, wherein said housing is made of a material that has a low X-ray absorption in relation to said plurality of calibration materials.

8. An apparatus as recited in claim 7, wherein said plurality of calibration materials comprises materials that have atomic numbers and densities that are similar to the atomic numbers and densities of the materials in said test material.

9. An apparatus for providing data for the calibration of the atomic number and density of a test material being scanned in the radiation field of a computerized axial tomographic scanner (CAT), said apparatus comprising: a housing adapted to be positioned in said radiation field in a predetermined position adjacent said test material; and a plurality of calibration materials having known atomic numbers and densities positioned in said housing.

10. An apparatus as recited in claim 8, wherein said housing comprises a table.

11. An apparatus as recited in claim 9, wherein said test material comprises a human body.

12. An apparatus as recited in claim 8, wherein said plurality of calibration materials comprises a plurality of rods.

13. An apparatus as recited in claim 8, wherein said plurality of calibration materials comprises a plurality of vials containing a plurality of fluids.

14. An apparatus as recited in claim 8, wherein said housing is made of a material that has a low X-ray absorption in relation to said plurality of calibration materials.

15. An apparatus as recited in claim 8, wherein said housing comprises a cylinder.

16. An apparatus as recited in claim 9, wherein said predetermined position of said housing is stationary within said radiation field and said test material is moveable.

17. An apparatus as recited in claim 8, wherein said plurality of calibration materials are at least as long as said test materials.

18. An apparatus as recited in claim 17, wherein said plurality of calibration materials comprises materials that have atomic numbers and densities that are similar to the atomic numbers and densities of the materials in said test material.

19. An apparatus as recited in claim 18, wherein said housing comprises a table and said test material comprises a human body.

* * * * *